United States Patent
Reitan et al.

(10) Patent No.: US 7,250,059 B2
(45) Date of Patent: Jul. 31, 2007

(54) MYRINGOPEXY TYPE TITANIUM PROSTHESIS

(75) Inventors: Harlan J. Reitan, Collierville, TN (US); Michael D. White, Olive Branch, MS (US)

(73) Assignee: Clarity Corporation, Memphis, TN (US)

( * ) Notice: Subject to any disclaimer, the term of this patent is extended or adjusted under 35 U.S.C. 154(b) by 0 days.

(21) Appl. No.: 10/940,515

(22) Filed: Sep. 14, 2004

(65) Prior Publication Data
US 2006/0058875 A1    Mar. 16, 2006

(51) Int. Cl.
*A61F 2/18* (2006.01)
*A61B 19/00* (2006.01)
*H04R 25/00* (2006.01)
*A61N 1/00* (2006.01)

(52) U.S. Cl. .......................... 623/10; 128/898; 600/25; 607/55

(58) Field of Classification Search ............... 128/898; 623/10; 600/25; 607/55, 137
See application file for complete search history.

(56) References Cited

U.S. PATENT DOCUMENTS

| | | | | |
|---|---|---|---|---|
| 4,450,593 A | * | 5/1984 | Poler | 623/6.4 |
| 4,704,126 A | * | 11/1987 | Baswell et al. | 623/10 |
| 6,524,340 B2 | * | 2/2003 | Israel | 623/6.44 |
| 2002/0045939 A1 | * | 4/2002 | Kurz | 623/10 |
| 2003/0130734 A1 | * | 7/2003 | Antonelli et al. | 623/10 |
| 2004/0162614 A1 | * | 8/2004 | Steinhardt et al. | 623/10 |

FOREIGN PATENT DOCUMENTS

EP    1054573    * 11/2000

OTHER PUBLICATIONS

M.W. Yung, Ph.D., F.R.C.S., D.L.O., C. Brewis, F.R.C.S., "A Comparison of the User-Friendliness of Hydroxyapatite and Titanium Ossicular Prostheses". The Journal of Laryngology & Otology, Feb. 2002, vol. 116, pp. 97-102.

* cited by examiner

*Primary Examiner*—David J. Isabella
(74) *Attorney, Agent, or Firm*—Wood, Phillips, Katz, Clark & Mortimer

(57) ABSTRACT

A middle ear prosthesis comprises a one piece disk shaped prosthesis including a generally circular malleable body including a bore. The body engages a tympanic membrane and the bore receives a head of a stapes when implanted in a middle ear. More particularly, the middle ear prosthesis comprises a body comprising an annular head, a collar, and a plurality of radially extending members connecting the head to the collar. The head engages a tympanic membrane and the collar receives a head of a stapes when implanted in a middle ear.

18 Claims, 3 Drawing Sheets

MYRINGOPEXY TYPE TITANIUM PROSTHESIS

FIELD OF THE INVENTION

This invention relates to an ossicular prosthesis used for replacement and reconstruction and, more particularly, to a myringopexy type prosthesis.

BACKGROUND OF THE INVENTION

Due to disease, trauma, or congenital malformation, the ossicles of the middle ear are sometimes damaged. Pexy is a medical term which generally refers to fixation. Myringo is a medical term generally referring to the ear drum. Myringopexy is a condition where the ear drum becomes fixed to the ossicles. More specifically, myringostapediopexy is a condition where the eardrum is fixed to the stapes with the stapes acting like a columella. Retraction of the ear drum occurs when negative pressure builds up in the middle ear from eustachian dysfunction. Specifically, the tube that leads from the ear to the back of the nose no longer passes air into the middle ear. Under such conditions, a retraction pocket can form in the eardrum and eventually the pocket may turn up skin, forming a skin cyst or cholesteatoma. The entire eardrum collapses and drapes over the bones of the middle ear. Further progression of retraction pockets can cause erosion of the middle ear bones or ossicles. While a ventilation tube is the first corrective step for retraction of the eardrum, in more severe cases a prosthesis may be needed to replace damaged bones.

The distance where a prosthesis may be used can be anywhere from 0.5 mm to 1 mm. Existing middle ear prosthesis used for myringopexy indications require major modifications at the time of surgery. This is because the length of the prosthesis is far too long for the distance between the eardrum and the mobile stapes. It is not uncommon that even when a prosthesis is modified, it is still too long to place between the eardrum and stapes. Additionally, existing prostheses are currently made from materials that are heavy or lack support.

One known prosthesis is mushroom-shaped having an enlarged head and a shaft. The current method of modifying such a prosthesis for myringopexy is to cut the shaft of the prosthesis as short as possible. Additionally, notches in the shaft may need to be added to better fit over the stapes. The current material of choice for such a prosthesis is Plasti-Pore which can be easily cut and shaped. Plasti-Pore is porous polyethylene which permits tissue ingrowth into the interconnecting pores of the implant material. Because of the sponge like characteristics of Plasti-Pore, sound conduction is dampened compared to using a more rigid material. A surgeon may also opt to use just the head or platform of a hydroxylapatite prosthesis. In such a case the shaft which is affixed to the hydroxylapatite head must be removed at the time of surgery. Alternatively, the head can be sold independently. Hydroxylapatite is a ceramic based material that closely mimics natural bone. However, weight of the material can be a concern.

The present invention is directed to improvements in a myringopexy type prosthesis.

SUMMARY OF THE INVENTION

In accordance with the invention, there is provided a myringopexy type prosthesis formed of a malleable body.

Broadly, there is disclosed in accordance with one aspect of the invention, a middle ear prosthesis comprising a one piece disk shaped prosthesis comprising a generally circular malleable body including a bore. The body engages a tympanic membrane and the bore receives a head of a stapes when implanted in a middle ear.

It is a feature of the invention that the bore comprises a through bore.

It is another feature of the invention that the body comprises a titanium body.

It is a further feature of the invention that the body comprises a ring, a hub and spokes connecting the ring to the hub. The hub may comprise a tubular hub having opposite arch-shaped notches to align with arches of the stapes.

It is still another feature of the invention that the body is cannulated on opposite sides of the bore to provide visibility of the stapes during implantation.

There is disclosed in accordance with another aspect of the invention a middle ear prosthesis comprising a body comprising an annular head, a collar, and a plurality of radially extending members connecting the head to the collar. The head engages a tympanic membrane and the collar receives a head of a stapes when implanted in a middle ear.

It is a feature of the invention that the plurality of radially extending members comprise a pair of aligned, malleable radially extending members to enable the head to be tilted relative to the collar.

It is another feature of the invention that diameter of the head is relatively large compared to height of the collar.

It is still another feature of the invention that an axis of the collar is perpendicular to a plane of the head.

In accordance with another aspect of the invention, there is disclosed the method of treating myringopexy comprising: removing an incus and malleus of a middle ear; providing a one piece disk shaped prosthesis comprising a generally circular malleable body including a bore; aligning the prosthesis with a stapes so a head of the stapes is received in the bore; and releasing a tympanic membrane so that it collapses on the body to retain the prosthesis in the middle ear.

Further features and advantages of the invention will be readily apparent from the specification and from the drawings.

DETAILED DESCRIPTION OF THE INVENTION

Figure 1:
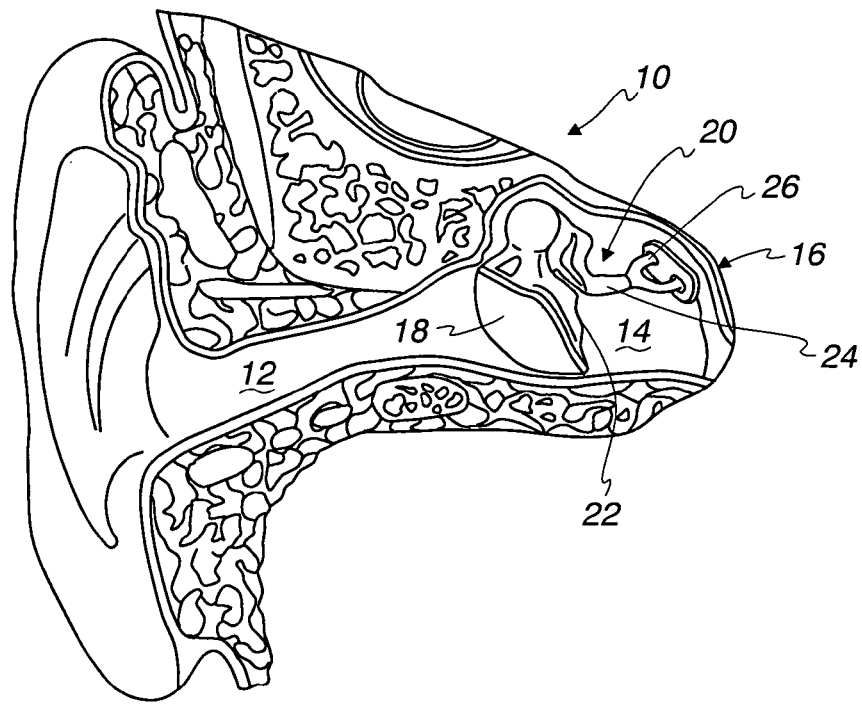
FIG. 1 is perspective, partial cross section view of the anatomy of an ear showing a normal ossicular chain.
Figure 6:
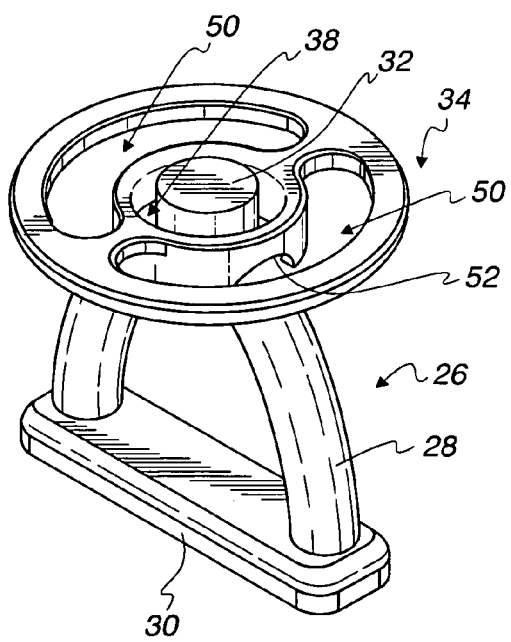
FIG. 6 is a perspective view illustrating aligning the prosthesis of FIG. 3 on a stapes.

Referring initially to FIG. 1, a human ear 10 includes an external or outer ear 12, a middle ear 14 and an inner ear 16. A tympanic membrane 18, also called the ear drum, separates the outer ear 12 from the middle ear 14. The middle ear 14 includes an ossicular chain 20 comprising three small bones that are connected and transmit the sound waves from the ear drum 18 to the inner ear 16. The three small bones are called the malleus 22, the incus 24, and the stapes 26. Referring to FIG. 6, the stapes 26 includes a loop or arch 28 connected to a footplate 30. A head 32 at the top of the arch 28 connects to the incus 24.

Figure 2:
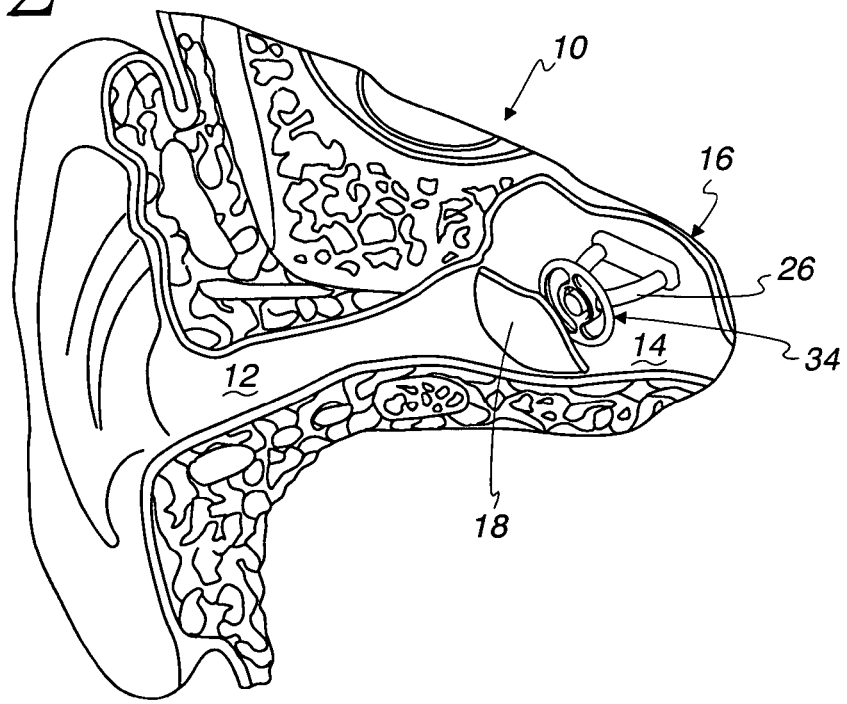
FIG. 2 is a view, similar to that of FIG. 1, showing the middle ear with part of the ossicular chain removed and replaced with a prosthesis in accordance with the invention.

In accordance with the invention, a prosthesis 34 is used for treating myringopexy. The procedure for treating myringopexy in accordance with the invention is for a surgeon to initially remove the incus 24 and malleus 22. This leaves only the stapes 26 in the middle ear 14, as shown in FIG. 2. The prosthesis 34 is aligned with the stapes 26 to be received thereon. The tympanic membrane 18 can then be released so that it collapses on the prosthesis 34 to retain the prosthesis 34 in the middle ear 14.

Figure 3:
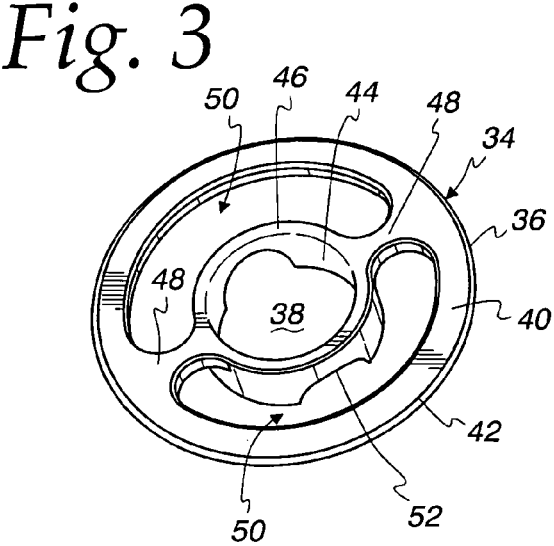
FIG. 3 is a perspective view of the prosthesis in accordance with the invention.
Figure 4:
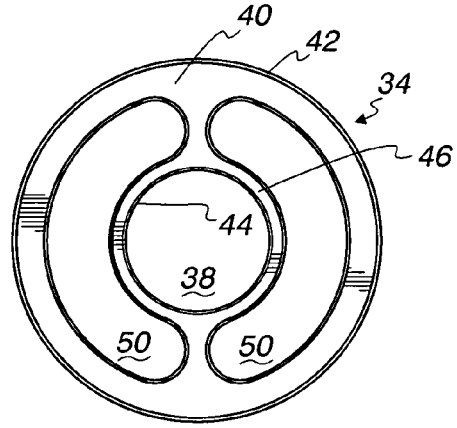
FIG. 4 is a plan view of the prosthesis of FIG. 3.
Figure 5:
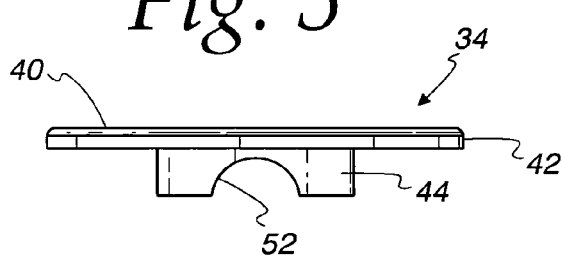
FIG. 5 is an elevation view of the prosthesis of FIG. 3.

Referring to FIGS. 3-5, the prosthesis 34 is illustrated. The prosthesis 34 comprises a one piece disk shaped body 36. Particularly, the body 36 comprises a generally circular malleable body including a bore 38. The body 36 engages the tympanic membrane 18 and the bore 38 receives the stapes head 32 when implanted in a middle ear 14. In the illustrated embodiment of the invention, the bore 38 comprises a through bore. The body 36 is formed of titanium. Advantageously, the body is made of a softer grade titanium, such as, for example, ASTM F67 grades 1 or 2.

More particularly, the body 36 comprises an annular ring 40 defining a head or platform. An outer edge of the ring 40 is turned downwardly at 42 to provide a smooth edge for engaging the tympanic membrane 18. A generally tubular collar or hub 44 defines the through bore 38. An upper edge of the hub 44 comprises a flange 46 coplanar with the ring 40. A pair of radially extending members, or spokes 48, connect the ring 40 to the hub 44. The body is cannulated on opposite sides of the hub 44, formed by arc shaped openings 50. The tubular hub 44 includes opposite arch shaped notches 52 opposite the flange end 46.

Figure 7:
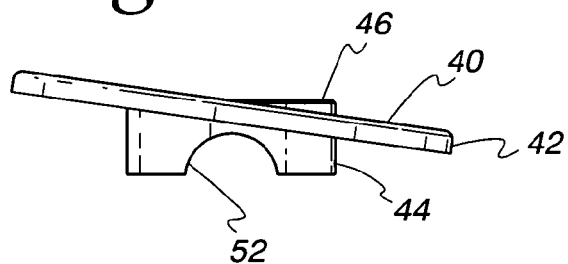
FIG. 7 is an elevation view, similar to FIG. 5, illustrating a head of the prosthesis tilted relative to the collar.
Figure 8:
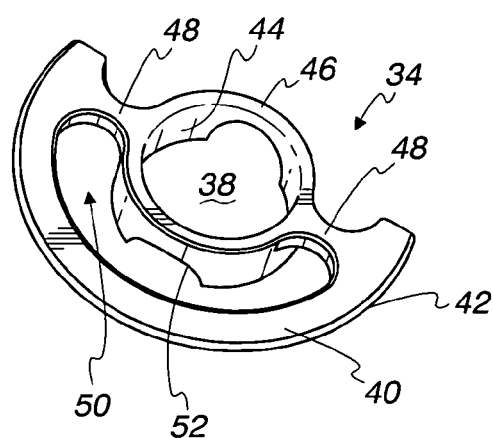
FIG. 8 is a perspective view of the prosthesis of FIG. 3 with part of a head trimmed to fit a middle ear.
Figure 9:
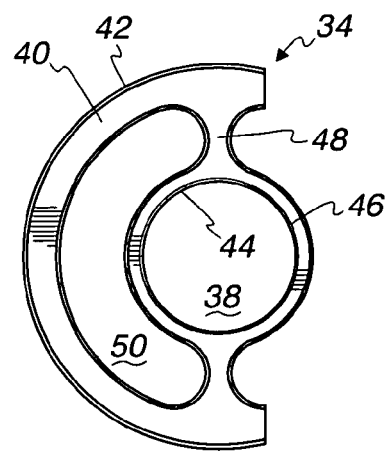
FIG. 9 is a plan view of the prosthesis of FIG. 8.

The body 36 is approximately 3.0 mm in diameter and has a height of approximately 0.5 mm to provide a disk shape. The canulation provided by the openings 50 provides maximum visibility of the stapes 26 and footplate 30 during surgery. The malleability of the titanium enables each side of the ring 40 to be bent and/or tilted along an axis of the spokes 48, as shown in FIG. 7 according to the patient's anatomy. The arch cut outs or notches 52 anatomically align with the arches 28, as shown in FIG. 6. Flexibility is provided by the head design which can be trimmed such as by removing a portion of the ring 40, as shown in FIGS. 8 and 9 to custom fit the patient. Titanium is considered a superior implant material because it weighs less than other implant materials and conducts sound vibrations well.

Referring specifically to FIGS. 2 and 6, during implantation, the prosthesis 34 is aligned with the stapes 26. The stapes head 32 is received in the bore 38. The notches 52 rest on the arches 28. The openings 50 provide visibility for the surgeon to see the arches 28 and foot plate 30 during implantation. According to the anatomy of the particular ear, the ring 40 can be bent, can be tilted as shown in FIG. 7, or can be trimmed as shown in FIGS. 8 and 9. Further, the body 36 can be covered with cartilage so that the tympanic membrane 18 rests on the cartilage, rather than the body 36. The body 36 floats on the cartilage, while the cartilage can grow into the tympanic membrane 18. The negative ear pressure causes the ear drum 18 to collapse onto the prosthesis 34 to provide pressure contact. The tension of the tympanic membrane 18 relative to the stapes head 32 sandwiches the prosthesis 34 to maintain it in position.

Thus, in accordance with the invention, there is provided a one piece disk shaped titanium prosthesis used for treating myringopexy. The prosthesis is designed for flexibility and stability and is lightweight and provides good sound conduction.

We claim:

1. The method of treating myringopexy comprising:
   removing an incus and malleus of a middle ear;
   providing a one piece disk shaped prosthesis comprising a generally circular malleable body including a bore;
   aligning the prostheses with a stapes so a head of the stapes is received in the bore; and
   releasing a tympanic membrane so that it collapses on the body to retain the prosthesis in the middle ear.

2. The method of claim 1 wherein the body comprises a titanium body.

3. The method of claim 1 wherein the body comprises a tubular hub defining the bore and the hub comprises opposite arch shaped notches and wherein aligning the prostheses with a stapes comprises positioning arches of the stapes in the notches.

4. The method of claim 1 wherein the body comprises an annular head, a collar, and a plurality of radially extending members connecting the head to the collar and further comprising bending the radially extending members to tilt the head relative to the collar.

5. The method of claim 1 wherein the body comprises an annular head, a collar, and a plurality of radially extending members connecting the head to the collar and further comprising trimming the head to fit a middle ear.

6. The method of claim 5 wherein the body comprises an annular head, a collar, and a plurality of radially extending members connecting the head to the collar and the plurality of radially extending members comprise a pair of aligned, malleable radially extending members to enable the head to be tilted relative to the collar.

7. The method of implanting a middle ear prosthesis in the absence of an incus and malleus of the middle ear comprising:
   providing a one piece disk shaped prosthesis comprising a generally circular malleable body including a bore; and
   aligning the prostheses with a stapes so a head of the stapes is received in the bore and the tympanic membrane collapses on the body to retain the prosthesis in the middle ear.

8. The method of claim 7 wherein the body comprises a titanium body.

9. The method of claim 7 wherein the body comprises a tubular hub defining the bore and the hub comprises opposite arch shaped notches and wherein aligning the prostheses with a stapes comprises positioning arches of the stapes in the notches.

10. The method of claim 7 wherein the body comprises an annular head, a collar, and a plurality of radially extending members connecting the head to the collar and further comprising bending the radially extending members to tilt the head relative to the collar.

11. The method of claim 7 wherein the body comprises an annular head, a collar, and a plurality of radially extending members connecting the head to the collar and further comprising trimming the head to fit a middle ear.

12. The method of claim 11 wherein the body comprises an annular head, a collar, and a plurality of radially extending members connecting the head to the collar and the plurality of radially extending members comprise a pair of aligned, malleable radially extending members to enable the head to be tilted relative to the collar.

13. A middle ear prosthesis comprising:
a one piece prosthesis comprising a malleable disk shaped head and a hub disposed within the head and at least partially coplanar with the head, the head for engaging a tympanic membrane and the hub for receiving a head of a stapes when implanted in a middle ear, the hub being of a length so that a portion of the stapes head is coplanar with the head after implantation.

14. The middle ear prosthesis of claim 13 wherein the head has a thickness of about 0.5 mm.

15. The middle ear prosthesis of claim 13 wherein the body comprises a titanium body.

16. The middle ear prosthesis of claim 13 wherein the head comprises a ring and wherein spokes connect the ring to the hub.

17. The middle ear prosthesis of claim 16 wherein the hub comprises a tubular hub having opposite arch shaped notches to align with arches of the stapes.

18. The middle ear prosthesis of claim 13 wherein the head is cannulated on opposite sides of the hub to provide visibility of the stapes during implantation.

* * * * *